United States Patent [19]
Sieben et al.

[11] Patent Number: 5,833,688
[45] Date of Patent: Nov. 10, 1998

[54] SENSING TEMPERATURE WITH PLURALITY OF CATHETER SENSORS

[75] Inventors: Wayne Sieben, Mendata Hgts., Minn.; Alan Oslan, Watertown, Mass.

[73] Assignee: Boston Scientific Corporation, Natick, Mass.

[21] Appl. No.: 804,824

[22] Filed: Feb. 24, 1997

[51] Int. Cl.⁶ .................................................. A61B 17/39
[52] U.S. Cl. ................... 606/41; 606/15; 606/45
[58] Field of Search ..................... 606/41, 42; 600/549; 607/99, 102, 122; 374/166, 179, 181, 183, 185, 141; 338/25

[56] References Cited

U.S. PATENT DOCUMENTS

| | | | |
|---|---|---|---|
| 4,403,296 | 9/1983 | Prosky | 364/573 |
| 4,966,597 | 10/1990 | Cosman | 606/50 |
| 5,281,212 | 1/1994 | Savage et al. | 605/15 |
| 5,423,805 | 6/1995 | Brucker et al. | 605/15 |
| 5,582,609 | 12/1996 | Swanson et al. | 606/39 |
| 5,588,438 | 12/1996 | McKown et al. | |
| 5,599,345 | 2/1997 | Edwards et al. | 606/41 |
| 5,685,878 | 11/1997 | Falwell et al. | 606/49 |

FOREIGN PATENT DOCUMENTS

WO 96/00039  1/1996  WIPO.
WO 96/34558  11/1996  WIPO.

OTHER PUBLICATIONS

Husng et al., "Temperature Guided Radiofrequency Catheter Abiation of the Canine Ventricular Myocardium—a Pilot Evaluation of a Prototype of Thermistor—Tipped Electrode Catheter," *Circulation*, 84(4):2 (Oct. 1991).

Blouin et al. "Assessment of Effects of a Radiofrequency Energy Field and Thermistor Location in an Electrode Catheter on the Accuracy of Temperature Measurement," *Pace*, 14:807–813 (May 1991).

Calkins et al. "Temperature Monitoring During Radiofrequency Catheter Ablation Procedures Using Closed Loop Control," *Circulation*, 90(3):1279–1286 (Sep. 1994).

Haines et al. "Monitoring Electrode Tip Temperature During Radiofrequency Fulguration of Ventricular Myocardium is strongly Predictive of Lesion Size," *Circulation*, 76 (Oct., 1987).

Langberg et al. "Temperature Monitoring During Radiofrequency Catheter Ablation of Accessory Pathways," *Circulation*, 80(5):1469–1474 (Nov., 1992).

*Primary Examiner*—John P. Lacyk
*Assistant Examiner*—Roy D. Gibson
*Attorney, Agent, or Firm*—Lyon & Lyon LLP

[57] ABSTRACT

A dual temperature sensor assembly is used in an ablation catheter. The sensor assembly includes a thermistor and a thermocouple. The ablation catheter has a body with a distal end and a proximal end. An ablation member (e.g., an electrode for providing energy) is disposed at the distal end of the body for ablating tissue. The sensor assembly allows the ablation catheter to be used with any known generator/controller unit, either the thermistor-based kind or the thermocouple-based kind.

23 Claims, 5 Drawing Sheets

SENSING TEMPERATURE WITH PLURALITY OF CATHETER SENSORS

TECHNICAL FIELD

This invention relates to catheters and, more particularly, to ablation catheters capable of sensing temperature by using at least two temperature sensors of different types in or on an ablation catheter.

BACKGROUND INFORMATION

Cardiac arrhythmia is an electrical malfunction of the heart. Electrophysiological therapy treats cardiac arrhythmia by ablating the tissue area that is the source of the electrical malfunction. To ablate the tissue, a physician performing the electrophysiological therapy steers an ablation catheter through a vein or an artery into the interior region of the heart. The catheter has an ablating element (e.g., an electrode or a fiber optic) along the distal end of the catheter which delivers energy (e.g., radio frequencies or laser light) to the targeted tissue. The delivered energy heats the tissue and forms a lesion. Temperature is a critical parameter in achieving success with the procedure. The lesion size and shape are a function of the temperature of the ablated tissue, the surrounding tissue, and/or the ablating element. Thus, temperature is monitored during the procedure. The catheter includes a temperature sensor to measure the temperature of the tissue near the ablating element during the procedure. It is known to use a thermistor or a thermocouple at the end of the catheter to measure the temperature.

The ablation catheter typically is connected to a controller/generator unit by a medical grade cable with an adapter specific to the controller/generator unit. The generator delivers the energy necessary for ablation and the controller receives temperature-related signals from the thermistor or the thermocouple. The controller may further monitor electrical activity of the heart during the ablation procedure. The controller and the generator can be a single unit, or the two functions can be performed by two separate units.

Radio frequency (RF) energy is one type of ablating energy used in electrophysiological therapy. The RF ablation generator/controller units currently available are either thermistor-based or thermocouple-based. That is, known RF generator/controller units can display temperature based on signals provided by a temperature sensor in the catheter, but they can do so only for a particular type of temperature sensor, either a thermistor or a thermocouple. Therefore, a different catheter design must be developed and provided depending on the type of generator/controller unit with which the catheter will be used. The following commercially-available RF generator/controller units for medical applications are thermistor-based: EPT 1000; Osypka HAT-200S; Osypka HAT-300S; and Radionics RFG-3E. Two commercially-available thermocouple-based RF generator/controller units available for medical applications are Medtronic Atakr and Radionics RFG-3D.

SUMMARY OF THE INVENTION

The invention relates to using at least two temperature sensors of different types in or on a catheter. The different types of temperature sensors sense and detect temperature according to different physical principles. One of the temperature sensors can be a thermocouple, and the other sensor can be another type of temperature sensor such as a thermistor.

According to the invention, a thermocouple and a thermistor are incorporated in a catheter such that the catheter is compatible with both varieties of generator/controller units, a thermistor-based and thermocouple-based. Given appropriate coupling, a catheter equipped with the two temperature sensors can function properly with generator/controller units designed to work with catheters having only thermocouples and with generator/controller units designed to work with catheters having only thermistors. The invention thus eliminates the need for catheter providers to design or develop both a catheter for use with thermistor-based generator/controller units and a different catheter for use with thermocouple-based generator/controller units. Furthermore, a catheter equipped with temperature sensors of different types provide more accurate measurements by allowing the operator to compare measurements from one type against another.

The two types of temperature sensors can be packaged in a single sensor assembly, and the sensor assembly may be placed in a variety of locations at the distal end of the catheter body. In an alternative embodiment, the two types of temperature sensors may be disposed at the distal end of the catheter body as separate, individual sensors rather than as a single sensor assembly.

The single sensor assembly with the two temperature sensors, according to the invention, can have a three-conductor configuration. In this configuration, three conductors extend along the length of the catheter body from the proximal end thereof to the sensor assembly. One of the three conductors extends to the thermistor, a second one of the conductors extends to the thermocouple, and the third conductor extends to and is common to both the thermistor and the thermocouple. This common-conductor arrangement allows three conductors to be used instead of four, and thus reduces fabrication complexity and cost of the sensor assembly.

In one aspect, the invention features a catheter comprising a catheter body and at least two temperature sensors of different types. The catheter body has a distal end and a proximal end. The two temperature sensors are disposed at the distal end of the catheter for sensing temperature. A thermocouple and a thermistor are the two temperature sensors of different types.

In another aspect, the invention involves a temperature sensor assembly for use in a catheter. The sensor assembly comprises a thermocouple, a thermistor, and an insulator within which the thermistor and the thermocouple are disposed. A first conductor extends to the thermistor, a second conductor extends to the thermocouple, and a third conductor extends to and is common to both the thermistor and the thermocouple. The first, second, and third conductors extend to the insulator, and the second and third conductors comprise dissimilar metals.

In yet another aspect, the invention relates to a method of sensing temperature. The method comprises providing a catheter with two temperature sensors and a controller, coupling one of the two temperature sensors to the controller, sensing temperature with the temperature sensor coupled to the controller and providing temperature indications. The catheter comprises a catheter body with a distal end and a proximal end, and two dissimilar temperature sensors disposed at the distal end of the catheter body for sensing temperature. One of the two dissimilar of temperature sensors comprises a thermistor and the other comprises a thermocouple. The controller provides temperature indications and is operable with either a thermistor-based catheter or a thermocouple-based catheter. The controller provides temperature indications based on signals from either the thermistor or the thermocouple, depending on which one the controller is coupled to.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figures 1, 2:
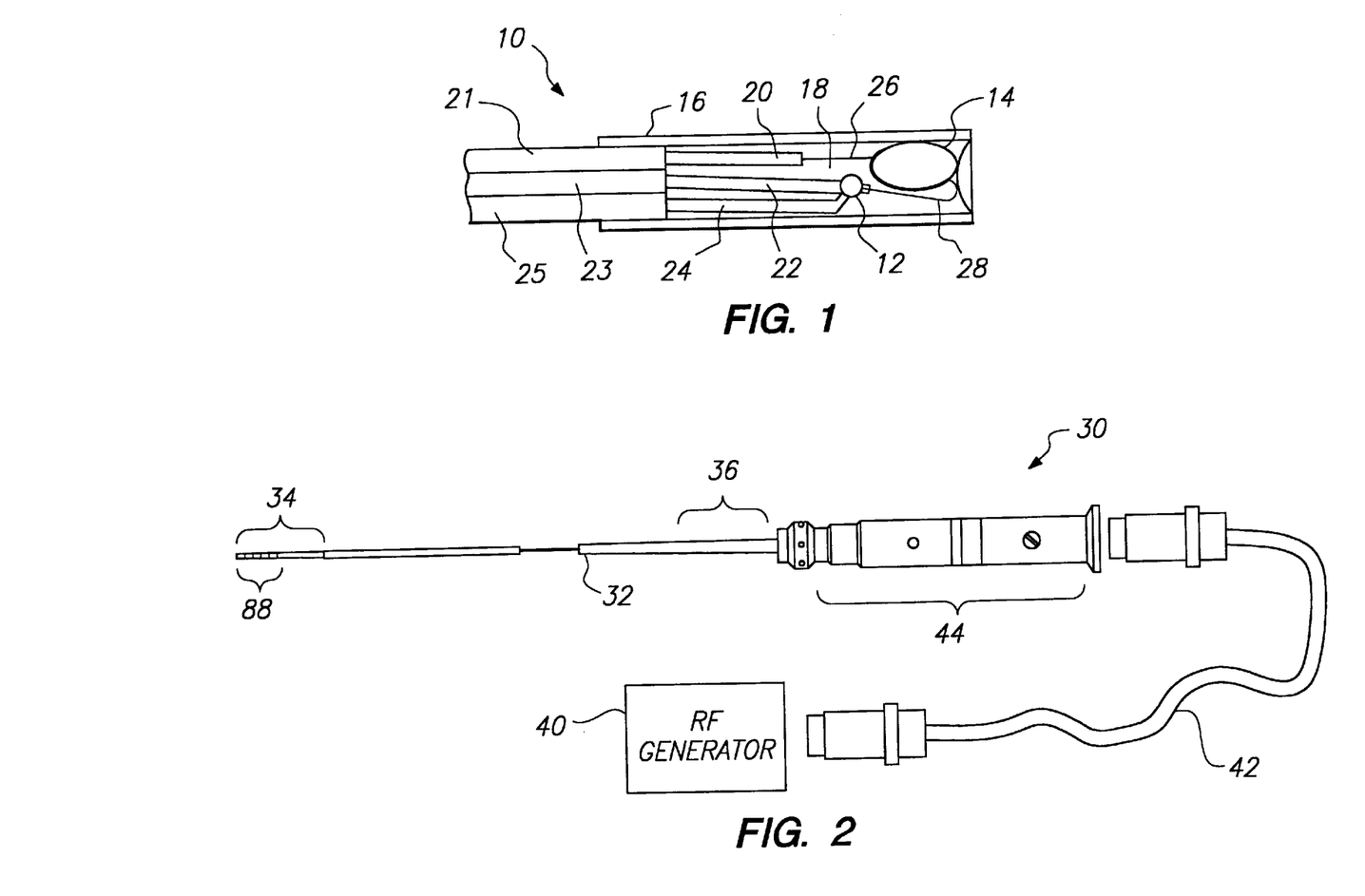
FIG. 1 is a diagram of a sensor assembly according to the invention.
FIG. 2 is a diagram of an RF ablation catheter coupled to an RF generator/controller units.

In accordance with the invention, at least two temperature sensors of different types are included in a catheter used in medical applications. The two types of sensors detect temperature during a medical procedure performed with the catheter. Referring to FIG. 1, a dual temperature sensor assembly 10 designed for use in an ablation catheter according to the invention includes a thermocouple 12 and a thermistor 14. The thermocouple 12 and the thermistor 14 are the two temperature sensors, and each senses and detects temperature according to a different physical principle. In general, the thermocouple 12 is a temperature sensing device that produces an electrical output voltage which changes predictably with temperature, and the thermistor 14 is a temperature sensing device that produces an electrical resistance which changes predictably with temperature.

Referring still to FIG. 1, the disclosed embodiment of the sensor assembly 10 according to the invention further includes an insulator sleeve 16 around the thermocouple 12 and the thermistor 14 for electrically insulating the at least two temperature sensors from, for example, an electrode of the catheter. In the disclosed embodiment, the insulator sleeve 16 is made of polymide, although it generally can be made of any sufficiently insulating material. The insulating sleeve is electrically insulating yet thermally conducting. The thermocouple 12 and the thermistor 14 are potted (with a thermally conducting potting 18) inside the insulator sleeve 16 to secure their positions. The potting 18 and the sleeve 16 together form a strain relief arrangement which keeps the at least two temperature sensors 12, 14 secure in the event conductors 20, 22, 24 extending beyond the sleeve 16 are pulled or twisted. The three conductors 20, 22, 24 are strands of metal with insulation 21, 23, 25 surrounding each strand external to the sleeve 16, and the three conductors generally extend the length of the catheter when the sensor assembly 10 is installed in or on the catheter. The thermocouple 12 and the thermistor 14 share the second conductor 22. The first conductor 20 extends to only the thermistor 14, and the third conductor 24 extends to only the thermocouple 12. In the disclosed embodiment, the first and second conductors 20, 22 comprise a similar metal, and the third conductor 24 comprises a different metal.

In the disclosed embodiment, the thermocouple 12 is formed by coupling the second and third conductors 22, 24 which are dissimilar metals, and the coupling can be accomplished by forming a welded bead at the junction of the two dissimilar metals 22, 24. The thermocouple 12 senses and detects temperature by measuring the voltage difference between the second conductor 22 and the third conductor 24. The voltage increases with the increase in temperature at the junction. The physical principle upon which the operation of the thermocouple 12 is based is as follows. When the area at or near the junction between two dissimilar metals is heated, electrons leave one metal and travel to the other metal to occupy a lower energy state. As the electrons leave, excess positive and negative charges are built and a potential difference is generated at the junction. Various combinations of dissimilar metals can be used to form the thermocouple 12. In a type T thermocouple, copper is electrically coupled to constantan. The thermocouple 12 of the sensor assembly 10 of FIG. 1 is a type T thermocouple. Other variations include a type E thermocouple where nickel-10% chromium is electrically coupled to constantan, a type K thermocouple where nickel-10% chromium is electrically coupled to nickel 5% aluminum silicon, a type J thermocouple where iron is electrically coupled to constantan, a type R thermocouple where platinum-13% rhodium is electrically coupled to platinum, and a type S thermocouple where platinum-10% rhodium is coupled to platinum.

In the disclosed embodiment, the thermistor 14 is a semiconductor bead, rod, or disk. The thermistor 14 has two leads 26, 28 which are coupled to the first and second conductors 20, 22 by, for example, soldering. The thermistor 14 senses and detects temperature by measuring electrical resistance. The semiconductor material of which the thermistor 14 is made has a resistance which varies with temperature due to the semiconductor material's high temperature coefficient of resistance.

While embodiments of the invention having at least two temperature sensors 12, 14 packaged within the same assembly 10 have been described above with reference to FIG. 1, and will be described in other figures below, it is possible for other embodiments of the invention to be configured in a different manner. For example, a thermistor and a thermocouple may be housed in a single assembly in a manner different from the one shown in FIG. 1. Any embodiment of the invention will include at least two temperature sensors of different types for use with a catheter to sense and detect temperature. An alternate embodiment of the invention thus can include a thermistor and a thermocouple in or on a catheter, but not housed in the same or a single sensor assembly. For example, the thermistor could be placed at a certain point at a distal end of the catheter, and the thermocouple could be placed at a different point at the distal end of the catheter.

In the disclosed embodiment, each of the at least two temperature sensors 12, 14 of the sensor assembly 10 is capable of sensing temperature in the range of 20° C. to 120° C.

In one embodiment, an ablation catheter includes the dual sensor assembly. The ablation catheter may obtain energy needed for ablation from an electromagnetic, radiation, mechanical or thermal energy source. Electromagnetic energy sources include light such as laser, radio frequency and microwave energy.

In a preferred embodiment, a radio frequency (RF) ablation catheter equipped with the sensor assembly 10 (i.e., with both the thermocouple 12 and the thermistor 14) is compatible with either type of commercially-available RF generator/controller unit, a thermocouple-based or a thermistor-based. A thermocouple-based RF generator/controller unit will provide temperature indications derived from signals sent thereto by a temperature sensor in an RF ablation catheter but only if the sensor is a thermocouple, and a thermistor-based RF generator/controller unit will provide temperature indications derived from signals sent thereto by a temperature sensor in an RF ablation catheter but only if the sensor is a thermistor. With the dual temperature sensor assembly 10 of the invention, a single catheter design employing the sensor assembly 10 can be used effectively with either type of RF generator/controller unit. The invention thus eliminates the need for catheter designers, manufacturers, and/or sellers to provide two separate versions of each catheter, a thermocouple-equipped version and a thermistor-equipped version, because the dual temperature sensor assembly 10 includes both types of temperature sensors in a single catheter. Therefore, a hospital or other treatment facility having both thermistor-based RF generator/controller units and thermocouple-based RF generator/controller units no longer needs catheters of two different designs, and the user at the hospital or facility need not worry about whether he or she has the proper type of catheter to match the RF generator/controller unit that will be employed in the ablation procedure.

Referring to FIG. 2, an RF ablation catheter 30 includes a catheter body 32 with a distal end 34 and a proximal end 36. In the disclosed embodiment, the length of the body 32 is about 110 cm to 120 cm, although other lengths are possible. A plurality of ablation members 38 at the distal end 34 of the catheter body 32 deliver RF energy generated by an RF generator/controller unit 40. The ablation members 38 in the disclosed embodiment are electrodes for delivering RF energy to ablate tissue. One or more of the dual temperature sensor assemblies 10 of FIG. 1 also are disposed at the distal end 34 of the catheter body 32. If more than one sensor assembly 10 is used in the catheter 30, each assembly 10 could be located at or near each of the electrodes 38. The three conductors 20, 22, 24 extending to each sensor assembly 10 run the length of the catheter body 32 and through a handle 44 of the catheter. To perform an ablation, the RF generator/controller unit 40 is coupled to the ablation catheter 30 (and the sensor assemblies 10 of the catheter 30) with an appropriate adapter and a cable 42. The adapter and the cable 42 connect at least one of the at least two temperature sensors 12, 14 in the sensor assembly 10 to the RF generator/controller unit 40. If the RF generator/controller unit 40 is thermistor-based, all thermistors 14 in the sensor assemblies 10 are coupled to the RF generator/controller unit 40. If the RF generator/controller unit 40 is thermocouple-based, all thermocouples 12 in the sensor assemblies 10 are coupled to the RF generator/controller unit 40.

Figure 3:
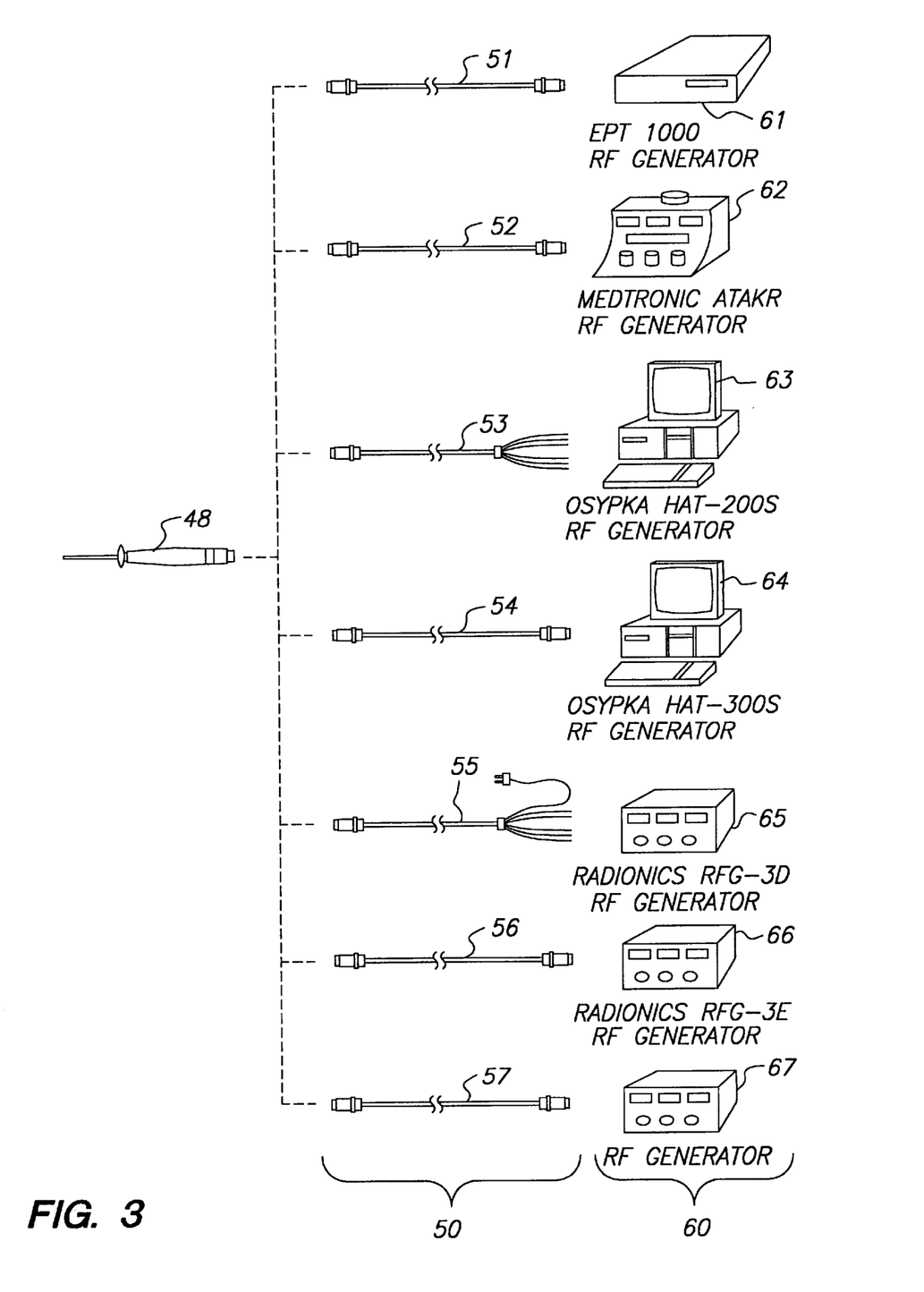
FIG. 3 is a diagram of different RF generator/controller units and associated adapter cables for coupling a catheter according to the invention with each of the different generator/controller units.

Referring to FIG. 3, different types of RF generator/controller units 60 can be coupled to an ablation catheter 30, 48 having the dual temperature sensor assembly 10, according to the invention. Typically, the ablation catheter 30 connects to an RF controller/generator unit 60 via a cable and an adapter. In one embodiment, the adapter may be designed to connect to a specific type of RF controller/generator unit 60 or to connect to a various types of RF controller/generator unit 60. Alternatively, if the catheter and the RF controller/generator unit 60 require differently shaped plugs, two adapters connected to each other, the second adapter designed specifically to plug to the controller/generator unit 60 can be used. In the embodiment disclosed in FIG. 3, various types of adapters and cables 50 are used to couple the ablation catheter 30, 48 to each of the different RF generator/controller units 60. An appropriate adapter, selected based on the type of RF generator/controller unit to be used, and a cable 51–57 couple the catheter 30, 48 to the RF generator/controller unit 61–67 such that either the thermocouple(s) 12 or the thermistor(s) 14 of the catheter 48 is/are coupled to the RF generator/controller unit and the RF energy can be transmitted from the RF generator/controller unit to the electrodes at the distal end of the catheter.

Figure 4A:
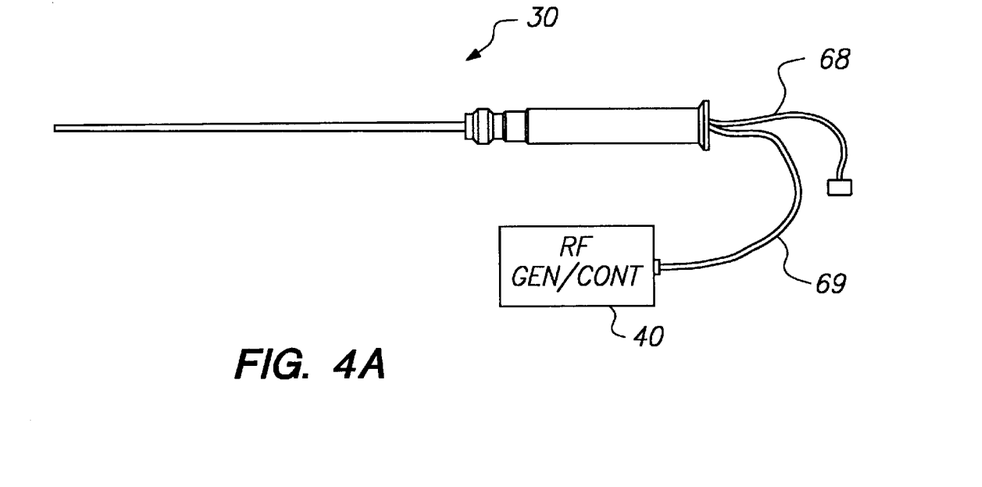
FIG. 4A is a diagram of a catheter with separate cables for each type of temperature sensors.
Figure 4B:
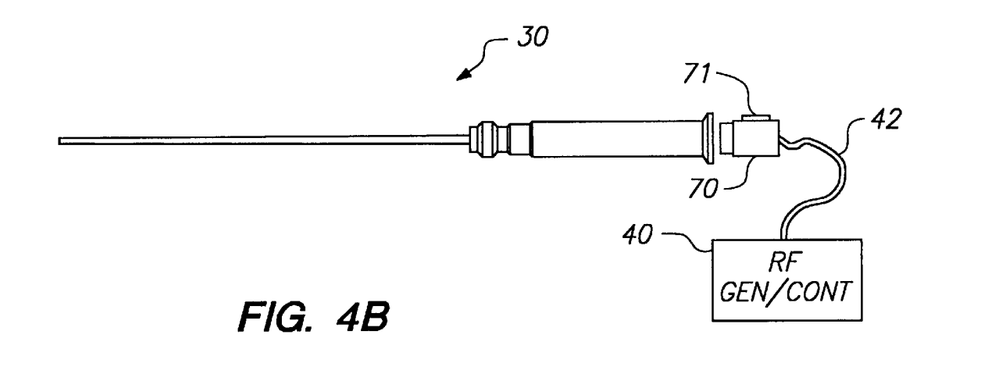
FIG. 4B is a diagram of a catheter coupled to an adapter with a switch for choosing the desired sensor type.
Figure 4C:
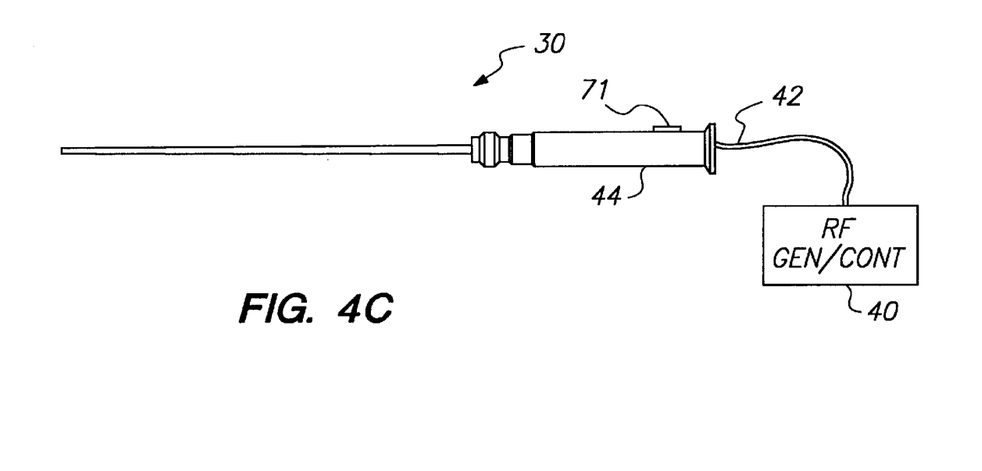
FIG. 4C is a diagram of a catheter with a switch on the handle for choosing the desired sensor type.

The ablation catheter of the invention can incorporate one of the following options to allow the operator to choose the desired sensor type. Referring to FIG. 4A, two cables 68, 69 are connected to the catheter 30, one cable 68 to the thermistors in the catheter 30 and the other cable 69 to the thermocouples in the catheter 30. With this option, the operator connects only one of these cables 68, 69 to the RF generator/controller unit 40 when using the device. Referring to FIG. 4B, the catheter 30 is connected to a single cable 42 and an adapter 70 with a switch 71 which allows the operator to choose the thermocouples or the thermistors. Depending on the switch 71 indication, only one type of sensor is coupled to the RF generator/controller unit 40. Alternatively, a cable may be connected to two adapters where the second adapter, by design connects to the desired sensor type. Referring to FIG. 4C, instead of the adapter, the catheter handle 44 has a switch 71 to select the right sensor type.

The dual temperature sensor assembly 10 of the invention has uses and advantages beyond those described above. It is possible, given the proper generator/controller unit, to receive and process signals from both of the two different types of temperature sensors 12, 14 in the sensor assembly 10. Such a configuration could be useful to check the two different temperature sensors 12, 14 against each other to make sure each is providing accurate and reliable temperature information back to the generator/controller unit.

In accordance with the invention, the dual temperature sensor assembly or the plurality of separate temperature sensors may be placed in a variety of locations at the distal end of an ablation catheter body. The following factors are relevant to determining where to locate the individual temperature sensors or the sensor assembly in or on the catheter. First, it is important to note that in tissue ablation the shape and size of a lesion created by emission of energy to the targeted tissue are closely related to the temperature of the ablated tissue region, and thus it is critical to monitor the temperature of the region during an ablation procedure. The amount of ablation energy released can be adjusted in accordance with temperature readings to achieve a lesion of the desired shape and size. Second, the temperature at the interface of the tissue and the ablating electrode is not the hottest region during an ablation procedure. The hottest region during ablation generally is located within the tissue being ablated at a depth of about 0.5 mm to 2.9 mm from the electrode-tissue interface, and thus a temperature sensor would have to be inserted into the tissue being ablated to monitor the hottest region. In general, acceptable accuracy and results can be achieved in a tissue ablation procedure by measuring the temperature at or near the electrode-tissue interface without actually inserting a temperature sensor into the tissue being ablated.

Figure 5:
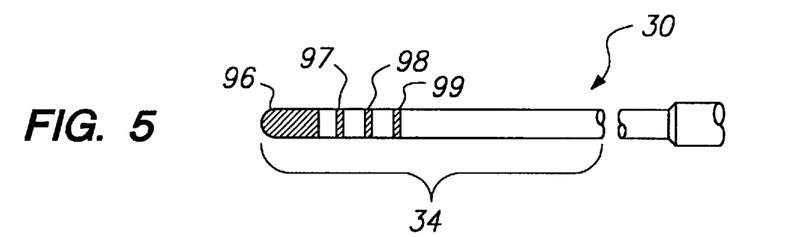
FIG. 5 is a diagram of a distal end of an ablation catheter comprising a tip electrode and ring electrodes.
Figure 6A:
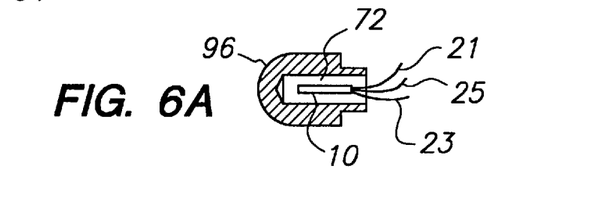
FIGS. 6A and 6B are diagrams in cross-section of the placement of a sensor assembly according to the invention in an ablation catheter.
Figure 6B:
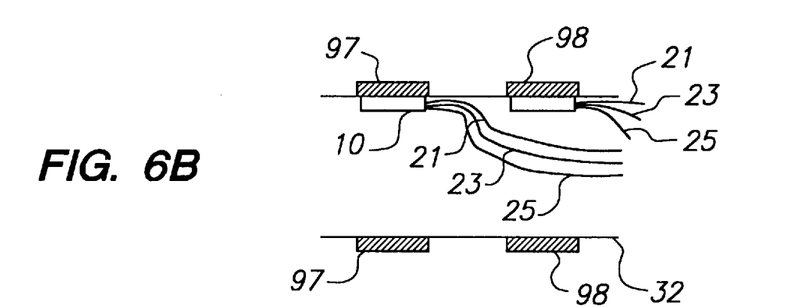

Referring to FIG. 5, in a disclosed embodiment of the RF ablation catheter 30, a tip electrode 96 and a plurality of ring electrodes 97, 98, 99 are disposed at the distal end 34 of the catheter 30. As shown in PIG. 6A, the sensor assembly 10 of the invention can be disposed within the tip electrode 96. As shown in FIG. 6B, as an alternative, or in addition, to disposing the sensor assembly 10 within the tip electrode 96, the sensor assembly 10 can be disposed within the catheter body 32 near one or more of the ring electrodes 97, 98, 99.

With the sensor assembly 10 disposed within the tip electrode 96 (FIG. 6A), the approximate temperature of the ablated tissue region is being measured via a measurement of the ablating tip electrode 96. When using the placement depicted in FIG. 6A, good thermal contact between the sensor assembly 10 and the tip electrode 96 is required, and such contact can be achieved by using a thermally conducting and electrically insulating material 72 to pot the sensor assembly 10 within the tip electrode 96. The potting material 72 can be, for example, a cyanoacrylate such as LOCTITE product no. 4013 or other suitable material.

With the sensor assembly 10 disposed within the catheter body 32 near one or more ring electrode 97, 98, 99 (FIG. 6B), the approximate temperature of the ablated tissue region is being measured via a measurement of the ring electrode(s) 97, 98, 99. When using the placement depicted in FIG. 6B, good thermal contact between the sensor assembly 10 and the ring electrode is required, and such contact can be achieved by using a thermally conducting and electrically insulating adhesive material to adhere the sensor assembly 10 to the ring electrode. The adhesive material can be, for example, a urethane methacrylate such as LOCTITE product no. 3021 or other suitable material.

Figure 7A:
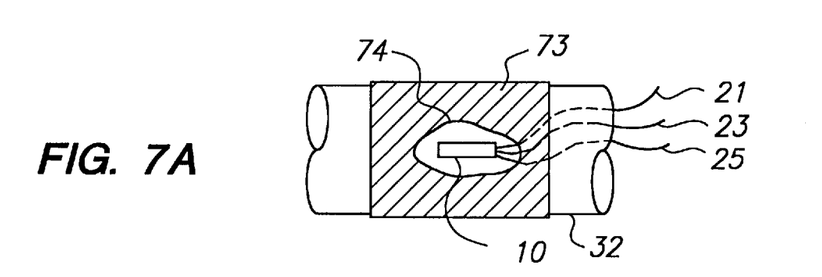
FIG. 7A and 7B are diagrams in cross-section of the placement of a sensor assembly according to the invention in an ablation catheter.

Another way to detect the temperature of the ablated tissue region is to have one or more of the temperature sensors actually contact the tissue. Referring to FIG. 7A, in a disclosed embodiment of the ablation catheter 30, at least one ring electrode 73 has an opening 74 leading to the exterior of the catheter body 32, and the dual temperature sensor assembly 10 is disposed within the opening 74. With this configuration depicted in FIG. 7A, it may be desirable to provide a thermal break between the sensor assembly 10 and the ring electrode 73 for more accurate temperature measurement, since the ring electrode 73 itself is indirectly heated by the ablated tissue and acts as a large heat sink exposed to flowing blood which acts as a convector. An example of a thermal break is a thermally and electrically insulating coating such as polytetrafluroethylene.

Figure 7B:
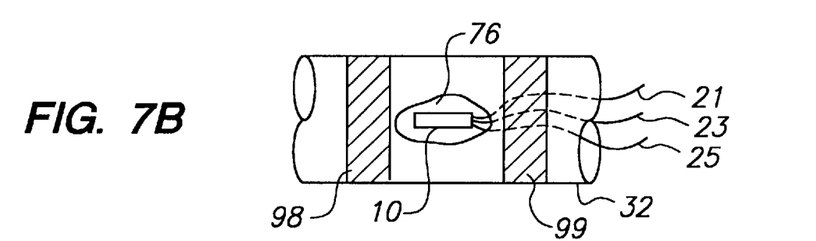

Still another way to detect the temperature of the ablated tissue region is to dispose one or more of the temperature sensors at the distal end 34 of the catheter body 32 in between two of the ring electrodes 97, 98, 99 as depicted in FIG. 7B. In this disclosed embodiment of the ablation catheter 30, the catheter body 32 has an opening 76 leading to the exterior of the catheter body 32, and the dual temperature sensor assembly 10 is disposed within the opening 76.

While certain placement locations for the dual temperature sensor assembly 10 have been disclosed above, it is possible to dispose individual temperature sensors and/or one or more of the sensor assemblies 10 in still other locations in or on the catheter body. In general, sensors may be placed in any locations that result in temperature readings sufficient to control acceptably the lesion size and shape.

Further details of a particular embodiment of the RF ablation catheter 30 are disclosed hereinafter with reference to FIGS. 8 and 9.

Figure 8:
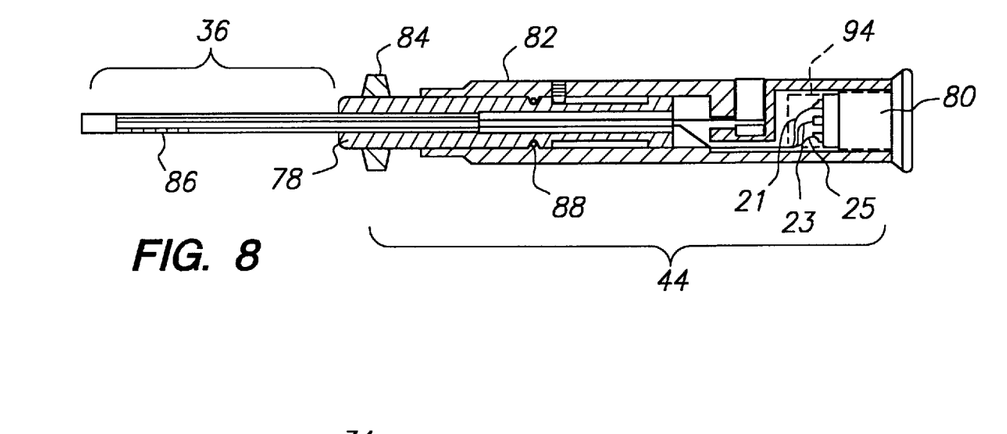
FIG. 8 is a diagram in cross-section of a proximal end of an ablation catheter including a handle.

Referring to FIG. 8, the proximal end 3 6 of the catheter body 32 extends from the handle 44 of the catheter 30. A movable piston body 78 and a connector 80 are located at either end of the handle 44, and a plastic sleeve 82 covers most of the handle 44. The connector 80 is used to connect the ablation catheter 3 0 to one of the RF generator/controller units 60 via one of the adapter cables 50. A thumb rest 84 surrounds the piston body 78. The proximal end 36 of the catheter body 32, which extends into the piston body 78, is enclosed in a heat shrinkable tube 86. An 0-ring 88 is disposed inside the piston body 78 to provide a seal as the piston body 78 moves in and out of the sleeve 82. The conductors 21, 23, 25 extending to the sensor assembly 10 at the distal end 34 of the catheter body 32 (and possibly other conductors extending to the electrodes at the distal end 34 of the catheter body 32 although only the three 21, 23, 25 are shown) through the catheter body 32 to the connector 80 are soldered to the connector 80. The soldered connections are surrounded with a heat shrinkable tube 94.

Figure 9:
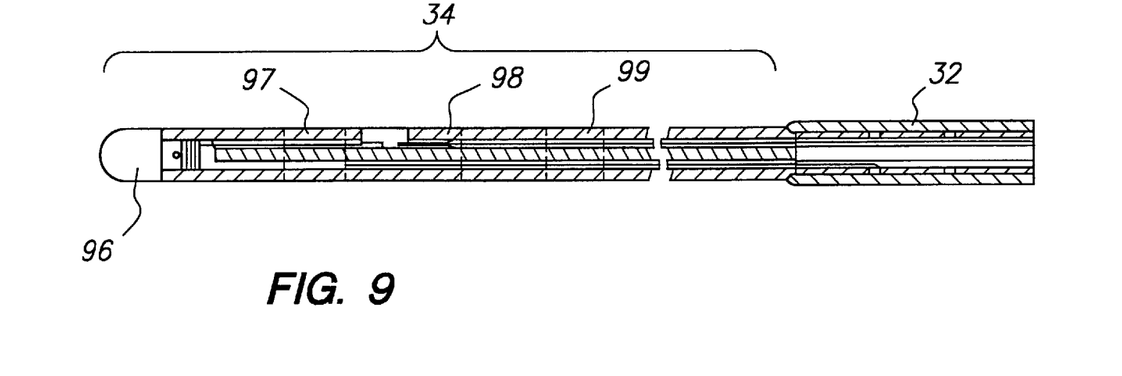
FIG. 9 is a diagram in cross-section of a distal end of an ablation catheter.

Referring to FIG. 9, the distal end 34 of the catheter body 32 has a smaller diameter than the rest of the rest of the catheter body 32. The approximate diameter of the distal end 34 of the catheter body 32 is 6.5 French. The diameter of the rest of the catheter body 32 is about 6.5 French to 7.0 French. The length of the distal end 32 of the catheter body 32 is about 6.2 cm to 7.2 cm. The distance between the tip electrode 68 and the ring electrodes 97, 98, 99 is about 1.3–2.3 mm, 7.4–8.4 mm, and 10.5–11.5 mm, respectively.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A catheter, comprising:
 a catheter body having a distal end and a proximal end; and
 at least two temperature sensors disposed at the distal end of the catheter body for sensing temperature, one of the temperature sensors comprising a thermistor and the other temperature sensor comprising a thermocouple.

2. The catheter of claim 1 wherein three conductors extend from the proximal end to the distal end of the catheter body, a first one of the conductors extending to the thermistor, a second one of the conductors extending to the thermocouple, and a third one of the conductors extending to and common to both the thermistor and the thermocouple.

3. The catheter of claim 1 wherein each of the at least two temperature sensors senses temperature in the range of 20° C. to 120° C.

4. The catheter of claim 1 wherein the thermocouple comprises a type T thermocouple.

5. The catheter of claim 2 wherein the second and third conductors comprise dissimilar metals.

6. The catheter of claim 5 wherein the second conductor comprises copper and the third conductor comprises constantan.

7. The catheter of claim 1 wherein the at least two temperature sensors are disposed in a thermally conductive, electrically insulative material.

8. The catheter of claim 7 wherein the thermally conducting insulator comprises polymide.

9. The ablation catheter of claim 1 wherein the length of the catheter body is about 110 cm to 120 cm.

10. The catheter of claim 1 further comprising an ablation member disposed at the distal end of the catheter body for providing energy to ablate tissue.

11. The catheter of claim 10 wherein the ablation member comprises at least one electrode.

12. The catheter of claim 11 wherein the at least one electrode comprises a tip electrode disposed at the tip of the distal end of the catheter body and wherein at least one of the at least two temperature sensors is disposed within the tip electrode.

13. The catheter of claim 11 wherein the at least one electrode comprises at least two ring electrodes disposed along the distal end of the catheter body and wherein at least one of the at least two temperature sensors are disposed between the two ring electrodes.

14. The catheter of claim 11 wherein the at least one electrode comprises at least one ring electrode and wherein at least one of the at least two temperature sensors is disposed within the catheter body near the ring electrode.

15. The catheter of claim 11 wherein the at least one electrode has an opening leading to the exterior of the catheter body and wherein at least one of the at least two temperature sensors is disposed within the opening.

16. The catheter of claim 11 wherein the at least one electrode provides radio frequency energy to ablate tissue.

17. The catheter of claim 10 wherein the ablation member provides laser energy to ablate tissue.

18. The catheter of claim 1 further comprising a controller and a coupler for coupling at least one of the two temperature sensors to the controller.

19. The catheter of claim 18 wherein the coupler comprises a handle connected to the proximal end of the catheter body, the handle including a switch configured to electrically couple one of the two temperature sensors to the controller.

20. The catheter of claim 18 wherein the coupler comprises a handle connected to the proximal end of the catheter body, the handle including a connector and an adapter connected to the connector wherein the adapter is configured to couple one of the two temperature sensors to the controller.

21. The catheter of claim 18 wherein the coupler comprises a handle connected to the proximal end of the catheter body, the handle including a connector and an adapter connected to the connector wherein the adapter comprises a switch configured to selectively couple one of the two temperature sensors to the controller.

22. A temperature sensor assembly for use in a catheter, comprising:
- a thermocouple;
- a thermistor;
- a first conductor extending to the thermistor;
- a second conductor extending to the thermocouple;
- a third conductor extending to and being common to both the thermistor and the thermocouple, the second and third conductors comprising dissimilar metals; and
- a thermally conductive, electrically insulative material within which the thermistor and thermocouple are disposed and to which the first, second, and third conductors extend.

23. A method of sensing temperature, comprising:
- providing a catheter comprising a catheter body having a distal end and, a proximal end and two dissimilar sensors disposed at the distal end of the catheter body for sensing temperature, one of the sensors comprising a thermistor and the other sensor comprising a thermocouple;
- providing a controller for providing temperature indications;
- coupling one of the two sensors to the controller; and
- sensing temperature with the sensor coupled to the controller and providing temperature indications with the controller.

* * * * *